US011598051B2

(12) United States Patent
Ekman et al.

(10) Patent No.: US 11,598,051 B2
(45) Date of Patent: Mar. 7, 2023

(54) METHOD FOR MANUFACTURING A FIBROUS WEB

(71) Applicant: Kemira Oyj, Helsinki (FI)

(72) Inventors: Jaakko Ekman, Helsinki (FI); Marko Kolari, Vantaa (FI); Juhana Ahola, Vantaa (FI)

(73) Assignee: Kemira Oyj, Helsinki (FI)

( * ) Notice: Subject to any disclaimer, the term of this patent is extended or adjusted under 35 U.S.C. 154(b) by 486 days.

(21) Appl. No.: 16/619,109

(22) PCT Filed: Jun. 19, 2018

(86) PCT No.: PCT/FI2018/050479
§ 371 (c)(1),
(2) Date: Dec. 4, 2019

(87) PCT Pub. No.: WO2018/234635
PCT Pub. Date: Dec. 27, 2018

(65) Prior Publication Data
US 2020/0095730 A1 Mar. 26, 2020

(30) Foreign Application Priority Data

Jun. 21, 2017 (FI) ..................................... 20175585

(51) Int. Cl.
| | | |
|---|---|---|
| D21H 21/04 | (2006.01) | |
| D21D 5/28 | (2006.01) | |
| D21H 21/36 | (2006.01) | |
| D21H 23/78 | (2006.01) | |
| D21C 5/00 | (2006.01) | |
| D21C 9/08 | (2006.01) | |
| G01N 33/18 | (2006.01) | |
| G01N 33/34 | (2006.01) | |

(52) U.S. Cl.
CPC .............. *D21H 21/04* (2013.01); *D21C 5/005* (2013.01); *D21C 9/08* (2013.01); *D21D 5/28* (2013.01); *D21H 21/36* (2013.01); *D21H 23/78* (2013.01); *G01N 33/18* (2013.01); *G01N 33/343* (2013.01)

(58) Field of Classification Search
CPC ........ D21H 21/04; D21H 21/36; D21H 23/78; D21D 5/28
See application file for complete search history.

(56) References Cited

U.S. PATENT DOCUMENTS

| | | | |
|---|---|---|---|
| 7,981,679 B2 | 7/2011 | Rice | |
| 9,157,189 B2 | 10/2015 | Heiskanen et al. | |
| 2014/0343872 A1* | 11/2014 | Ilmola ................. | G01N 33/1806 702/25 |
| 2017/0158537 A1 | 6/2017 | Buschmann | |

FOREIGN PATENT DOCUMENTS

| | | | |
|---|---|---|---|
| CN | 101245312 A | 8/2008 | |
| CN | 103842580 A | 6/2014 | |
| CN | 103959059 A | 7/2014 | |
| CN | 104936448 A | 9/2015 | |
| CN | 105050397 A | 11/2015 | |
| DE | 102013021893 A1 | 6/2015 | |
| EP | 1568384 A1 | 8/2005 | |
| EP | 3087035 B1 | 11/2017 | |
| FI | 126240 B | 8/2016 | |
| JP | 0938683 A * | 2/1997 | ............... C02F 3/12 |
| JP | 09038683 A * | 2/1997 | |
| RU | 2523312 C2 | 7/2014 | |
| RU | 2597619 C2 | 9/2016 | |
| SU | 1726252 A1 | 4/1992 | |
| WO | 2007125154 A1 | 11/2007 | |
| WO | 2008101089 A2 | 8/2008 | |
| WO | 2012070644 A1 | 5/2012 | |
| WO | 2012101051 A1 | 8/2012 | |
| WO | 2013026578 A1 | 2/2013 | |
| WO | 2013045325 A1 | 4/2013 | |
| WO | 2013079801 A1 | 6/2013 | |
| WO | 2013124542 A1 | 8/2013 | |
| WO | 2014114851 A1 | 7/2014 | |
| WO | 2014154946 A1 | 10/2014 | |
| WO | 2016135387 A1 | 9/2016 | |
| WO | 2017032927 A1 | 3/2017 | |

OTHER PUBLICATIONS

Robertson, Microbes in Papermachine Environment, 2011, PaperCon 2011 TAPPI (Year: 2011).*
Reichart et al., Redox potential measurement as a rapid method for microbiological testing and its validation for coliform determination, International Journal of Food Microbiology, 114, p. 143-148. (Year: 2007).*
Search Report of Corresponding Russian Patent Application No. 2019142688, dated May 20, 2021, 4 pages.
Finnish Patent and Registration Office, Search report of FI20175585, dated Jan. 26, 2018, 2 pages.

* cited by examiner

*Primary Examiner* — Anthony Calandra
(74) *Attorney, Agent, or Firm* — Meunier Carlin & Curfman LLC

(57) ABSTRACT

A method includes forming an aqueous fibre suspension including cellulosic fibres from one or more raw material flows, and applying at least one chemical and/or physical control measure to the aqueous fibre suspension or at least one of its raw material flows for control of microbial activity in the aqueous fibre suspension or the raw material flow before an inlet of an intermediate residence entity. In this manner a starting ORP value for the aqueous fibre suspension is obtained. The aqueous fibre suspension is in the intermediate residence entity at least a minimum delay time. A final ORP value is measured for the aqueous fibre suspension after an outlet of the intermediate residence entity before the formation of the fibrous web. An ORP difference value between the starting ORP and final ORP values is calculated. Finally, the aqueous fibre suspension is formed into a fibrous web and dried.

21 Claims, No Drawings

METHOD FOR MANUFACTURING A FIBROUS WEB

PRIORITY

This application is a U.S. national application of the international application number PCT/FI2018/050479 filed on Jun. 19, 2018 and claiming priority of Finnish application 20175585 filed on Jun. 21, 2017 the contents of all of which are incorporated herein by reference.

FIELD OF THE INVENTION

The present invention relates to a method for manufacturing a fibrous web according to the preamble of the enclosed independent claim.

BACKGROUND OF THE INVENTION

Bacterial cells are normally present in the aqueous environments of pulp mills as well as paper and board mills in form of vegetative cells, which multiply by cell division. Growth of the vegetative bacteria in the process is commonly monitored and limited by using various control measures, e.g. by feeding of biocides in the process. However, some genera of bacteria form endospores, which are highly resistant to typical destruction and control methods used for vegetative cells, such as heat, disinfectants, chemical biocides, desiccation, ultraviolet light and ionizing radiation. The transformation of bacterial cells from vegetative form into the resistant endospore form is called sporulation. Mature endospores may remain viable but dormant for prolonged periods, even for years, until the external conditions become favourable, after which the transformation, i.e. germination, of bacterial endospores back to vegetative form takes place.

The amount of vegetative cells and endospores in the final paper or board product should be as low as possible, especially if the product is intended for hygiene purposes, food or beverage packaging. Conventional manufacture of hygienic paper or board relies on intensive biocide treatment during furnish preparation and in the wet-end of the paper or board making process. The target of the conventional biocide treatment is to minimise or completely eliminate the vegetative bacterial cells and thus inhibit the endospore formation. However, this treatment requires high dosages of biocides which increases the process costs, and which may damage process equipment, e.g. cause corrosion. Furthermore, it has been observed that sometimes, even if the biocide dosage is high and the number of vegetative bacterial cells is low, the endospore count in the furnish is increased beyond acceptable levels. Consequently, there is a continuing need to inhibit the formation of endospores during pulp, paper or board manufacture.

SUMMARY OF THE INVENTION

It is an object of the present invention to reduce or even eliminate the above-mentioned problems appearing in prior art.

One object of the present invention is to provide a method with which the spore formation during the manufacture of paper, board or the like is minimised.

In order to realise the above-mentioned objects, among others, the invention is characterised by what is presented in the characterising part of the enclosed independent claim.

Some preferred embodiments according to the invention are disclosed in the dependent claims presented further below.

The embodiments mentioned in this text relate, where applicable, to all aspects of the invention, even if this is not always separately mentioned.

Typical method according to the present invention for manufacturing a fibrous web, such as web of paper, board, tissue or the like, comprises forming an aqueous fibre suspension comprising cellulosic fibres from one or more raw material flows, applying at least one chemical and/or physical control measure to the aqueous fibre suspension or at least one of its raw material flows for control of microbial activity in the aqueous fibre suspension or the raw material flow before an inlet of an intermediate residence entity, such as storage tower or broke tower, which has a minimum delay time of at least one hour, preferably at least two hours, and obtaining a starting ORP value for the aqueous fibre suspension, maintaining the aqueous fibre suspension in the intermediate residence entity at least the minimum delay time, measuring a final ORP value for the aqueous fibre suspension after an outlet of the said intermediate residence entity but before the formation of the fibrous web, calculating an ORP difference value between the starting ORP and final ORP values, and if the ORP difference value exceeds a pre-determined threshold value, then adjusting the applied chemical and/or physical control measure(s) until the ORP difference value falls below the threshold value, forming the aqueous fibre suspension into a fibrous web and drying the fibrous web.

DETAILED DESCRIPTION OF THE INVENTION

Now it has been surprisingly found that the endospore formation is effectively prevented when the ORP difference value between the starting ORP and final ORP values is maintained below a pre-determined threshold value. In practice this means that the applied control measures before the intermediate residence entity are adjusted to a level which inhibit excessive bacterial growth, but which do not fully eliminate the vegetative bacterial cells. In this manner the vegetative bacteria in the process are not induced by environmental stress to form endospores but remain as vegetative cells, which are easily destroyed by the heat in the drying section. The ORP difference value between starting and final ORP values of the aqueous fibre suspension provides a parameter with which the correct level of control measure(s) can be determined, maintained and if needed, adjusted. The final ORP value of the aqueous fibre suspension after the intermediate residence entity is maintained, with the help of the applied control measures on target level, wherein the ORP difference value between the starting ORP value and final ORP value is preferably less than 100 mV. In case the final ORP value deviates from the target level, and the ORP difference value between the starting and final ORP values exceeds the pre-determined threshold value, e.g. 100 mV, it is possible to adjust the applied control measure(s) before the intermediate residence entity in order to return the final ORP value back to the suitable target level and the ORP difference value falls below the threshold value.

The present invention thus aims to keep the bacteria in a vegetative state in the intermediate residence entity, whereby the endospore formation is minimised. There is no need for complete destruction of vegetative bacteria before the intermediate residence entity. The present invention minimises endospore formation as the stabile ORP difference value ensures that the bacteria are not subjected to environmental stress in the intermediate residence entity. In this manner the bacteria remain in vegetative form instead of forming endospores. The applied control measures are sufficient to prevent excessive bacterial growth in the intermediate residence entity, but they do not result in total elimination of bacteria.

The present invention enables also reduction of costs for control measures. For example, the amount of used biocidal compositions can be decreased as they are not added into the process system for complete or near complete destruction of vegetative bacterial cells. Further, the present invention improves the occupational safety and facilitates the compliance with biocide regulations when the excessive addition of biocides can be avoided. The present invention provides also advantages in view of general environmental and consumer concerns relating to the use of biocides.

In the present context the term "ORP value" denotes oxidation-reduction potential value of the aqueous fibre suspension. ORP value may be determined or measured by using an ORP probe, such as a redox electrode. These devices are known as such for a person skilled in the art, and not explained in more detail in this application.

The starting and/or final ORP value can be determined or measured continuously, or periodically, or at predetermined time intervals. According to one embodiment of the invention the final ORP value is measured continuously or more often than the obtained starting ORP value, i.e. at shorter intervals than the obtained starting ORP value. According to another embodiment both the starting and final ORP value are measured continuously.

The measured starting and final ORP values are used for calculation an ORP difference value, usually by simply subtracting the final ORP value from the starting ORP value, usually from the last measured starting ORP value. For the ORP difference value is pre-determined a threshold value, and the aim is to maintain the ORP difference below the threshold value.

The method according to the present invention is especially suitable for producing a hygienic fibrous web, such as hygienic web of paper, board, tissue or the like. In the present context the term "hygienic fibrous web" encompasses fibrous webs comprising cellulosic fibres, where bacterial endospore content in the dried web is less than about 1000 CFU/g, preferably less than about 500 CFU/g, more preferably less than about 250 CFU/g. The endospore content is preferably ≤1000 CFU/g, preferably 5500 CFU/g, more preferably 5250 CFU/g. According to one embodiment the hygienic fibrous web has a bacterial endospore content in the dried web <100 CFU/g, preferably <75 CFU/g, more preferably 50 CFU/g.

Aqueous fibre suspension is formed from a number of raw material flows, typically a plurality of raw material flows, such as water flow(s) and various pulp flows comprising cellulosic fibres. Raw material flows are combined together and form the aqueous fibre suspension which is fed to the intermediate residence entity. Microbial activity in the aqueous fibre suspension and/or at least one of its raw material flows is controlled by applying at least one chemical and/or physical control measure to the aqueous fibre suspension and/or at least one raw material flows to. For example, the aqueous fibre suspension may be subjected to an addition of a biocidal agent, which inhibits excessive growth of microorganisms in the aqueous fibre suspension. In addition, or alternatively, aqueous fibre suspension and/or its raw material flow may be subjected to a physical control measure, e.g. ultrasound or ultraviolet radiation. The control measure(s) may reduce the number of vegetative bacterial cells in the aqueous fibre suspension, but do(es) not eliminate them completely. The applied control measure may also only inhibit the activity or multiplying of the vegetative cells without reducing their actual amount. The control measure(s) is/are applied before the aqueous fibre suspension enters the intermediate residence entity.

The final ORP value for the aqueous fibre suspension that is used in the control of the process is measured after an outlet of an intermediate residence entity, but before the aqueous fibre suspension exits the headbox or the like and is formed into a web. The intermediate residence entity may be any pulp, water or broke storage tower or tank or corresponding entity, which has a minimum delay time of at least one hour, preferably at least two hours. Delay time is here understood as an average residence time for the aqueous fibre suspension in the intermediate residence entity. The endospore formation requires usually a minimum time, which means that the intermediate residence entities, especially with long delay times, are especially vulnerable points in view of endospore formation. The intermediate residence entity may have a delay time in the range of 1-12 h, typically 1-8 h, more typically 2-7 h. This means that the aqueous fibre suspension is maintained in the intermediate residence entity for 1-12 h, typically 1-8 h, more typically 2-7 h. Typically the consistency of the aqueous fibre suspension in the intermediate residence entity is at least 2 g/l, preferably in the range of 10-100 g/l.

The starting ORP value is determined before, or at the latest, at the inlet of the intermediate residence entity. If the aqueous fibre suspension is obtained by mixing of a plurality of raw material flows, such as water flow(s) and various pulp flows comprising cellulosic fibres, the starting ORP is usually determined after the mixing of all the raw material flows and preferably before the inlet of the intermediate residence entity. According to one embodiment of the invention, in case the process comprises a plurality of intermediate residence entities, such as storage towers, arranged in the series, the starting ORP value may be determined before or at the inlet of the first intermediate residence entity and the final ORP value is measured after the outlet of the last intermediate residence entity in the series, whereby the ORP difference value is calculated over the whole series of intermediate residence entities. The intermediate residence entities in the series may be different or similar to each other. Alternatively, a starting ORP value may be determined before the inlet of each intermediate residence entity and a final ORP value is measured after the outlet of each intermediate residence entity in the series and the ORP difference values are separately calculated for each intermediate residence entity, as well as the final ORP values are individually maintained on a target level for each intermediate residence entity. According to a further alternative, a critical intermediate residence entity in the series, e.g. with the longest delay time or with the most beneficial conditions for spore formation, is recognized and selected, whereafter the starting ORP value may be determined solely before the inlet of the critical intermediate residence entity and the final ORP value is measured solely after the outlet of the critical intermediate residence entity in the series and the ORP difference value is calculated for this critical intermediate residence entity and the final ORP value are maintained on a target level for the critical intermediate residence entity.

According to one preferable embodiment of the invention the ORP difference value is below the pre-determined threshold value at least for 90% of an observance period of 24 hours. For example, the final ORP value is maintained on the target level, i.e. on a level where the difference between the starting and final ORP value is <100 mV, at least for 90% of an observance period of 24 hours. In practice this means that under any observance period of 24 hours, when the process is working normally and excluding process start-ups, process down closings, cleaning periods, the calculated difference between the starting and final ORP value does not deviate for long periods and/or regularly over the pre-determined threshold value, e.g. 100 mV. Preferably, the ORP difference value is maintained below the pre-determined threshold value for at least 95%, more preferably at least for 97.5% of the observance period of 24 hours.

On basis of the calculated ORP difference value, based on the measured final ORP value of the aqueous fibre suspension, it is possible to adjust, if necessary, the chemical and/or physical control measure(s) to which the aqueous fibre suspension or at least one of its raw material flows is subjected prior to the intermediate residence entity. Chemical and/or physical control measure(s) may be applied until the ORP difference value falls below the pre-determined threshold value.

According to one preferable embodiment of the present invention the final ORP value may be in the predetermined range of 0-+350 mV, preferably 0-+200 mV, more preferably +50-+175 mV, even more preferably +100-+150 mV. The values are obtained by using conventional ORP electrodes comprising a platinum redox sensing electrode and a silver/silver chloride reference electrode in one body. It has been observed that the final ORP value within these predetermined ranges provides conditions where the microbial activity is controlled at a suitable level, avoiding anaerobic conditions, spore formation and/or excessive microbial growth. In case the final ORP value is inside the predetermined range, and the threshold value for ORP difference is not exceeded, no adjustment of the control measure(s) is necessary, but the adjustment may be done if deemed necessary on basis of other process parameters.

Also the obtained starting ORP value for the aqueous fibre suspension may be measured before its entry to the intermediate residence entity, i.e. before the inlet of the intermediate residence entity or at the inlet, at the latest. The starting ORP value does not only provide a starting level for the determination of the ORP difference value between the starting and final ORP values, but it is possible to use the starting ORP value for obtaining preliminary information about the effect of the control measure(s) applied on the aqueous fibre suspension and/or its raw material flows and/or changes in the properties of the aqueous fibre suspension itself. For example, the starting ORP value may provide preliminary information about the effect of the control measure(s) and/or appropriate level of the control measure(s).

The starting ORP value before the inlet of the intermediate residence entity and the final ORP value measured after the outlet of the intermediate residence entity are used to determinate the difference between the ORP values, i.e. the ORP difference value. The ORP difference value indicates the conditions prevailing in the intermediate residence entity. The pre-determined threshold value for ORP difference value may preferably be less than 100 mV. The pre-determined threshold value for the ORP difference value is less than 100 mV, preferably less than 90 mV, preferably 75 mV, more preferably less than 50 mV. The smaller the difference between the starting ORP value and the final ORP value, more stable are the conditions in the intermediate residence entity and smaller the risk for stressful environment leading to endospore formation.

According to one embodiment of the invention bacterial endospore content in the aqueous fibre suspension is determined after the intermediate residence entity. In this manner it can be guaranteed that there is no or only minimal endospore formation occurring in the intermediate residence entity and the applied control measures before the intermediate residence entity are at the appropriate level. According to one embodiment of the invention the aqueous fibre suspension may have a bacterial endospore content less than 400 CFU/ml, preferably less than 200 CFU/ml, more preferably less than 100 CFU/ml after the intermediate residence entity.

The pH of the aqueous fibre suspension may also be measured, before and/or after the intermediate residence entity. Preferably the pH of the aqueous fibre suspension is stable, around pH 7-9, and the maximum difference between the measured pH values is ±1 pH units. Stable pH reduces the risk for environmental stress factors and enables to keep the ORP value within the predetermined range.

According to one embodiment an rH value of the aqueous fibre suspension after the intermediate residence entity is in the range of 21-32, preferably 21-27, more preferably 22-26, even more preferably 24-26. The difference between aqueous fibre suspension's rH values before and after the intermediate residence entity may preferably be less than 3, preferably less than 2.5, more preferably less than 1.5 rH units. The rH value may be calculated from the pH and redox potential using equation (1):

$$rH = 2*pH + 2*Eh*F/(c.R.T) \qquad (1)$$

where
F=Faraday constant, $9.64853399(24) \times 10^4$ C mol$^{-1}$;
c=ln 10;
T=temperature, in Kelvin;
Eh=redox potential measured with standard hydrogen electrode, and
R=universal gas constant, 8.314472(15) J-K$^{-1}$ mol$^{-1}$.

It is possible to determine the bacterial endospore content value of the aqueous fibre suspension before and after the intermediate residence entity, whereby the difference between the determined endospore content values is preferably less than 100 CFU/ml, more preferably less than 75 CFU/ml. By determining the values for bacterial endospore content before and after the intermediate residence entity and their difference, information about the actual spore formation in the intermediate residence entity may be obtained. This determination is especially useful if the calculated ORP difference is near the pre-determined threshold value, or the measured ORP value(s) and/or other parameters are near the pre-determined border values or there is otherwise a suspicion about the actual conditions prevailing in the intermediate residence entity.

The aqueous fibre suspension is formed from cellulosic or lignocellulosic fibres, optional papermaking additives and water. The cellulosic fibres may be virgin fibres obtained by any known pulping process and/or they may be recycled fibres and/or they may originate from broke. For example, the fibre stock may comprise cellulosic fibres obtained by mechanical pulping, chemical pulping, chemithermomechanical pulping or by repulping recycled or recovered fibres. The cellulosic fibres can be refined or unrefined, bleached or unbleached. The cellulosic fibres may be recycled unbleached or bleached kraft pulp fibres, hardwood semi-chemical pulp fibres, grass pulp fibres or any mixtures thereof.

The aqueous fibre suspension may be formed by combining two or more raw material flows, which may comprise cellulosic fibres from different sources and/or fresh water and/or circulated process water. The chemical and/or physical control measure(s) may be applied to one or more of these raw material flows or to the aqueous fibre suspension after its formation.

The aqueous fibre suspension may contain one or several known chemical additives used in pulp and paper making.

According to one embodiment of the invention chemical control measure comprises feeding of a microbial control chemical to the aqueous fibre suspension or to at least one of its raw material flows. The microbial control chemical may be a biocide, reductive chemical or oxidative chemical.

According to one embodiment the biocide is non-oxidative biocide. Suitable non-oxidative biocide may selected from glutaraldehyde, 2,2-dibromo-3-nitrilopropionamide (DBNPA), 2-bromo-2-nitropropane-1,3-diol (Bronopol), carbamates, 5-chloro-2-methyl-4-isothiazolin-3-one (CMIT), 2-methyl-4-isothiazolin-3-one (MIT), 1,2-dibromo-2,4-dicyano butane, bis(trichloromethyl)sulfone, 2-bromo-2-nitrostyrene, 4,5-dichloro-1,2-dithiol-3-one, 2-n-octyl-4-isothiazolin-3-one, 1,2-benzisothiazolin-3-one, ortho-phthaldehyde, quaternary ammonium compounds (="quats"), such as n-alkyl dimethyl benzyl ammonium chloride, didecyl dimethyl ammonium chloride (DDAC) or alkenyl dimethylethyl ammonium chloride, guanidines, biguanidines, pyrithiones, 3-iodopropynyl-N-butylcarbamate, phosphonium salts, such as tetrakis hydroxymethyl phosphonium sulfate (THPS), dazomet, 2-(thiocyanomethylthio)benzothiazole, methylene bisthiocyanate (MBT), and a combination thereof. Preferably non-oxidative biocide is selected from glutaraldehyde, 5-chloro-2-methyl-4-isothiazolin-3-one (CMIT) and 2-methyl-4-isothiazolin-3-one (MIT).

According to another alternative the biocide may be an oxidative biocide, such as a stabilised active chlorine compound or a peracid. In one embodiment of the invention the oxidative biocide may include an oxidant, which is selected from chlorine, alkali and alkaline earth hypochlorite salts, hypochlorous acid, chlorinated isocyanurates, bromine, alkali and alkaline earth hypobromite salts, hypobromous acid, bromine chloride, chlorine dioxide, ozone, hydrogen peroxide, peroxy compounds, such as peracetic acid, performic acid, percarbonate or persulfate salts, halogenated hydantoins, e.g., monohalodimethylhydantoins such as monochlorodimethylhydantoin, or dihalodimethylhydantoins such as chlorobromo-dimethylhydantoin, monochloramines, monobromamines, dihaloamines, trihaloamines, or any combination thereof. It is further possible to combine the oxidant, preferably hypochlorite, with a nitrogen-containing compound in the oxidative biocide. Suitable nitrogen-containing compounds may be selected from ammonium salts, such as ammonium sulphate, ammonium bromide, ammonium chloride or ammonium carbamate, ammonia, urea, hydantoin, ethanolamine, pyrrolidone, 2-pyrrolidone, ethylene urea, N-methylolurea, N-methylurea, acetylurea, pyrrole, indole, formamide, benzamide, acetamide, imidazoline, or morpholine. According to one preferable embodiment oxidative biocide comprises urea or ammonium salts reacted with an oxidant, e.g. with hypochlorite salt. For example, oxidative biocide comprises urea, ammonium bromide, ammonium carbamate or ammonium sulphate which is reacted with an oxidant, e.g. hypochlorite. Preferable oxidative biocides are selected from monochloramine (MCA), chlorine dioxide, performic acid (PFA), peracetic acid, alkali and alkaline earth hypochlorite salts, and N-containing compounds combined with an oxidant, preferably hypochlorite. More preferably, oxidative biocides are selected from monochloramine (MCA), chlorine dioxide, performic acid, or a N-containing compound combined with an oxidant, e.g. urea reacted with an oxidant, such as hypochlorite.

The aqueous fibre suspension is formed into a fibrous web and dried in any suitable manner. The temperature during the drying is preferably at least 100° C., preferably at least 110° C., for at least 0.3 min, preferably at least 0.5 min, sometimes at least 1 min. This ensures the termination of vegetative bacterial cells and achievement of a hygienic fibrous web.

According to one embodiment the method for manufacturing a fibrous web, such as web of paper, board, tissue or the like, comprises forming an aqueous suspension comprising cellulosic fibres from one or more raw material flows, applying at least one chemical and/or physical control measure to the aqueous fibre suspension and/or at least one of its raw material flows for control of microbial activity in the aqueous fibre suspension and/or the raw material flow before an inlet of an intermediate residence entity, such as storage tower or broke tower, which has a delay time of at least one hour, preferably at least two hours, and obtaining a starting ORP value for the aqueous fibre suspension, measuring a final ORP value for the suspension after an outlet of the said intermediate residence entity but before the formation of a fibrous web, maintaining the final ORP value of the fibre suspension on a target level, where the difference between the starting and final ORP values is less than 100 mV, optionally by adjusting the applied chemical and/or physical control measure(s), forming the aqueous fibre suspension into the fibrous web and drying the fibrous web.

EXPERIMENTAL

Example 1

This laboratory test compared efficacy of two oxidizing biocides, namely free active chlorine and stabilized active chlorine, in killing of vegetative bacterial cells and in controlling of bacterial spore formation. Test was performed with authentic bacterial population of a broke sample taken from couch pit of a board machine making 3-ply food-packaging board. Broke sample was divided in equal proportions. Two reference samples were stored as such, the "free active chlorine" sample was treated with sodium hypochlorite, and the "stabilized active chlorine" sample was treated with sodium hypochlorite stabilized by 5,5-dimethylhydantoin (mixed in 1:1 molar ratio to form monochloro-5,5-dimethylhydantoin, MCDMH). Both forms of active chlorine were dosed at 10 ppm (=mg/l as total active chlorine $Cl_2$). Broke samples were stored at +45° C. without mixing. Total aerobic bacteria and aerobic bacterial spores were quantified by using conventional agar plate cultivation methods (Plate Count Agar, incubation at +37° C. for 2 days) at the beginning of the test (untreated reference samples) and after 1 and 2 days of contact time. Broke pH and Redox (mV) values were also monitored. Results are shown in Table 1.

Results in Table 1 show that in the beginning of the experiment the untreated reference broke samples 1 and 2 contained relatively low amounts of aerobic bacteria ($8\times10^2$ and $1\times10^3$ CFU/ml), and a small amount of aerobic bacterial spores (80 and 70 CFU/ml). During two days of storage the total aerobic bacteria level in the reference samples 1 and 2 increased up to $1-2\times10^7$ CFU/ml, whereas the aerobic bacterial spore counts decreased down to 10 and 30 CPU/ml. This indicates, surprisingly, that the aerobic storage conditions (pH 7.5-7.9, redox 120-149 mV) at a typical board machine temperature favoured vegetative bacterial growth but did not cause any increase in bacterial sporulation. Broke sample treated with free active chlorine (sodium hypochlorite, no stabilizer) showed almost equal content of vegetative bacteria after 1 day storage time. This indicates that at a 10 ppm dosing level the free active chlorine did not demonstrate any longer-term killing effect in the broke sample. However, the treatment with free active chlorine caused a 10-fold increase in the quantity of aerobic spores (60 CFU/ml→670 CFU/ml) due to the stress caused by the free active chlorine. Treatment of broke with a stabilized chlorine (MCDMH, 10 mg/l as active chlorine) showed 1 log unit stronger reduction of total aerobic bacteria content compared to free chlorine ($6\times10^4$ CFU/ml compared to $4\times10^5$ CPU/ml) after 1 day of storage. Further, the MCDMH did not cause any new spore formation in the broke and spore counts remained at 30-60 CPU/ml level during the 2 days experiment. After 2 days of storage all samples contained bacteria $1-2\times10^7$ CPU/ml indicating that none of the oxidizer treatments showed a long-lasting killing effect.

TABLE 1

Results of Example 1.

| | Start of the test | | | | 1 days storage time | | | | 2 days storage time | | | |
|---|---|---|---|---|---|---|---|---|---|---|---|---|
| | Total aerobic bacteria (CFU/ml) | Bacterial spores (CFU/ml) | pH | redox (mV) | Total aerobic bacteria (CFU/ml) | Bacterial spores (CFU/ml) | pH | redox (mV) | Total aerobic bacteria (CFU/ml) | Bacterial spores (CFU/ml) | pH | redox (mV) |
| Reference broke 1, no added Active Chlorine | $1\times10^3$ | 80 | 7.8 | 149 | $7\times10^5$ | 70 | 7.8 | 146 | $2\times10^7$ | 10 | 7.5 | 126 |
| Reference broke 2, no added Active Chlorine | $8\times10^2$ | 70 | 7.9 | 138 | $6\times10^5$ | 60 | 7.8 | 140 | $1\times10^7$ | 30 | 7.5 | 120 |
| Broke, Na-hypochlorite treatment, 10 mg/l | ND | ND | ND | ND | $4\times10^5$ | 60 | 7.8 | 108 | $2\times10^7$ | 670 | 7.6 | 68 |
| Broke, MCDMH treatment, 10 mg/l | ND | ND | ND | ND | $6\times10^4$ | 30 | 7.9 | 86 | $2\times10^7$ | 60 | 7.6 | 78 |

Example 1 shows, surprisingly, that a biocide treatment is not absolutely necessary for preventing bacterial spore formation in machine broke. Test demonstrated that if broke from of a board machine is stored under suitable conditions, the spore formation can be minimized. This example also showed that if such aerobic broke is treated with free active chlorine, at dosages not providing a complete kill of bacterial cells, it can irritate remaining bacteria to spore formation. Surprisingly, treating the broke in similar manner with stabilized active chlorine is not causing bacterial spore formation.

Example 2

This laboratory test was performed with broke sample taken from an alkaline board machine producing 3-ply food-packaging board and the sample included the mill's authentic bacterial population in it. The sample was divided in two different containers, one stored as such and the second one amended with biocide, 50 mg/l of glutaraldehyde as active agent. Containers were closed and stored at +45° C. without mixing i.e. under conditions that simulate situation in broke storage tower during a machine shutdown. Total aerobic bacteria and aerobic spore contents were determined by using conventional agar plate cultivation methods (plate count agar, 2 days incubation at +37° C.) at the beginning of the test and after 3 days of storage time, along with pH and redox measurements.

Results are shown in Table 2.

TABLE 2

Results of Example 2.

|  | At start of the test | | | | After 3 days storage time | | | |
|---|---|---|---|---|---|---|---|---|
|  | Total aerobic bacteria (CFU/ml) | Bacterial spores (CFU/ml) | pH | redox (mV) | Total aerobic bacteria (CFU/ml) | Bacterial spores (CFU/ml) | pH | redox (mV) |
| Untreated broke sample | $2 \times 10^7$ | 125 | 7.9 | 137 | $5 \times 10^7$ | 850 | 6.9 | −23 |
| Broke, treated with glutaraldehyde | ND | ND | ND | ND | $2 \times 10^7$ | 80 | 7.4 | 145 |

Results in Table 2 show that during 3 days of storage time, in the untreated broke sample, pH value (7.9→6.9) and redox value (+137 mV→−23 mV) dropped markedly indicating that conditions in the broke turned from aerobic to fermentative during the storage time. Total aerobic bacteria counts increased from 2×10⁷ CFU/ml to 5×10⁷ and amount of aerobic spores increased from 125 CFU/m to 850 CFU/ml.

Broke treated with 50 mg/l of glutaraldehyde biocide contained total aerobic bacteria 2×10⁷ CFU/ml after 3 days of storage, i.e. 40% of the untreated reference, indicating that this biocide treatment did not have a long-lasting killing effect. However, the treatment effectively prevented development of anaerobic fermentative conditions, i.e. redox (145 mV) and pH (7.4) remained at high level. Conditions were not triggering any spore formation in the broke sample and the broke contained only a low amount (80 CFU/ml) of spores after 3 days of storage.

Example 2 demonstrates that a biocide treatment which is not causing an intensive and long-lasting killing effect of bacterial cells can surprisingly well control spore formation in broke, as long as the biocide treatment is successful in preventing development of anaerobic conditions in the broke.

Example 3

This example compares technical performance of two different biocide programs in the broke system of a 3-ply board machine producing food-packaging board. Broke system is a part of the wet-end of the board making process. This board machine has set a hygiene target for the final board that it should contain aerobic bacterial spores less than 1000 CFU, and preferably less than 250 CFU, per gram of dry board.

In this experiment, for the first period (Days 1-10) the machine was running a biocide program consisting of stabilized active chlorine (MCDMH) and glutaraldehyde. For the second period, the machine was running chlorine dioxide, a non-stabilized oxidizer, as the biocide. It was running for 10 days starting from a shutdown (Days 15-25). Third period (Days 26-47) was run with the same MCDMH and glutaraldehyde program as the first period. During this experiment technical performance of the two different biocide programs was monitored at selected dates by several means: on-line Redox monitoring system collecting Redox values at every 10 minutes (results are shown as daily average mV values); measuring aerobic spore content of the final board samples; and by measuring aerobic bacterial spore quantities from different process locations by using agar plate cultivation methods (pasteurization at 82° C. for 20 min, followed by cultivation on Plate Count Agar for 2 days at +37° C.).

Results are shown in Table 3.

TABLE 3

Results of Example 3.

|  | | Aerobic Bacterial Spores (CFU/ml) in process | | | | Bacterial |
|---|---|---|---|---|---|---|
|  | Redox (mV) in Couch Pit (daily avg) | Low consistency (1-4 w/w-%) broke tower | High consistency (4-6 w/w-%) broke tower | ΔSpore content within the broke system | Incoming Pulp | Spores in Final Board (CFU/g) |
| Day 1 | 197 | 110 | 270 | +160 | 80 | 220 |
| Day 2 | 192 | 150 | 200 | +50 | 40 | 240 |
| Day 10 | 191 | 80 | 110 | +30 | 30 | 230 |
| Day 15 | 387 | 250 | 440 | +190 | 20 | 520 |
| Day 19 | 492 | 610 | 1100 | +490 | 60 | 5530 |
| Day 21 | 477 | ND | ND | ND | ND | 9580 |
| Day 25 | 471 | 850 | 950 | +100 | ND | 3210 |
| Day 43 | 186 | 280 | 210 | −70 | 40 | 680 |
| Day 47 | 173 | 50 | 170 | +120 | ND | 210 |

Results in Table 3 show that during the first period (Days 1-10) the produced final board had spore content always <250 CFU/g and thus the board met the hygiene targets. During days 1-10 redox level of couch pit (=tank collecting and sending material to low consistency broke tower) was stable at +190-200 mV range. It is seen that during days 1-10 the broke system had stable aerobic conditions and Δspore content within the broke system (=difference between inlet and outlet) was generally low, indicating that intensive formation of new spore did not occur. Also other areas of the process, treated with the stabilized oxidizer MCDMH, contained generally low amounts of spores. For example, pulp transportation water (15 CFU/ml) and incoming pulp (30-80 CFU/ml) possessed low quantities of spores, indicating that the MCDMH biocide program did not trigger intensive spore formation.

During second period (Days 15-25) the system was treated with chloride dioxide. Dosing of this non-stabilized oxidizer increased Redox values in the system dramatically, e.g. in broke system from +190 mV range up to +492 mV. Interestingly, spore quantities also showed a strong increase, for example up to 1100 CFU/ml in the high consistency broke tower. Also spore content in the final board increased dramatically, to a magnitude higher values than what is the set hygiene target for final board, the highest value being as high as 9580 CFU/g. This indicates that the strong oxidative stress caused by non-stabilized oxidizer triggered intensive spore formation in the broke system of this board machine.

During the third period (Days 26-47) the process was treated with MCDMH and glutaraldehyde, similarly as during the first period. With a small delay the process conditions stabilized back to similar Redox range as during first experimental period, and interestingly, also spore values in the final board returned back to target level.

Results from Example 3 support the surprising finding that for the production of food-packaging board with a low content of aerobic bacterial spores, it is more effective to treat the system with biocides such as stabilized-oxidizers and glutaraldehyde in a manner providing stable aerobic conditions with moderate Redox values, compared to treating the system with oxidizing biocides and targeting high +380 to +500 mV Redox values in the broke system.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for manufacturing a fibrous web, the method comprising:
    forming an aqueous fibre suspension comprising cellulosic fibres from one or more raw material flows;
    applying at least one chemical and/or physical control measure to the aqueous fibre suspension or at least one of its raw material flows for control of microbial activity in the aqueous fibre suspension or the raw material flow before an inlet of an intermediate residence entity; the intermediate residence entity having a minimum delay time of at least one hour;
    obtaining a starting ORP value for the aqueous fibre suspension, before or at the inlet of the intermediate residence entity and after the application of the at least one chemical and/or physical control measure;
    maintaining the aqueous fibre suspension in the intermediate residence entity at least the minimum delay time;
    measuring a final ORP value for the aqueous fibre suspension after an outlet of said intermediate residence entity but before a formation of the fibrous web;
    calculating an ORP difference value between the starting ORP and the final ORP values, and if the ORP difference value exceeds a predetermined threshold value, then adjusting the applied chemical and/or physical control measure(s) until the ORP difference value falls below the predetermined threshold value, wherein the predetermined threshold value for the ORP difference value is less than 100 mV; and
    forming the aqueous fibre suspension into a fibrous web and drying the fibrous web.

2. The method according to claim 1, wherein the ORP difference value is below the predetermined threshold value at least for 90% of an observance period of 24 hours.

3. The method according to claim 1, wherein the predetermined threshold value for the ORP difference value is less than 90 mV.

4. The method according to claim 3, wherein the predetermined threshold value for the ORP difference value is less than 75 mV.

5. The method according to claim 1, wherein the final ORP value is in a range of 0-+350 mV.

6. The method according to claim 5, wherein the final ORP value is in a range of +50-+175 mV.

7. The method according to claim 1, further comprising determining a first rH value of the aqueous fibre suspension after the intermediate residence entity, wherein the first rH value is in a range of 21-32.

8. The method according to claim 7, wherein the first rH value is in a range of 22-26.

9. The method according to claim 7, further comprising determining a second rH value for the aqueous fibre suspension before the intermediate residence entity, wherein a difference between the aqueous fibre suspension's rH values before and after the intermediate residence entity is less than 3.

10. The method according to claim 1, wherein after the intermediate residence entity, the aqueous fibre suspension has a bacterial endospore content less than 400 CFU/ml.

11. The method according to claim 10, wherein the aqueous fibre suspension has a bacterial endospore content less than 200 CFU/ml.

12. The method according to claim 1, further comprising determining a bacterial endospore content value of the aqueous fibre suspension before and after the intermediate residence entity, whereby a difference between the determined values is less than 100 CFU/ml.

13. The method according to claim 1, wherein a bacterial endospore content in the dried web is ≤1000 CFU/g.

14. The method according to claim 1, wherein the aqueous fibre suspension is maintained in the intermediate residence entity for 1-12 h.

15. The method according to claim 1, wherein the chemical control measure comprises feeding of a microbial control chemical to the aqueous fibre suspension or to at least one of its raw material flows.

16. The method according to claim 15, wherein the microbial control chemical is a biocide, a reductive chemical or an oxidative chemical.

17. The method according to claim 16, wherein the biocide is a non-oxidative biocide selected from glutaraldehyde, 5-chloro-2-methyl-4-isothiazolin-3-one (CMIT) and 2-methyl-4-isothiazolin-3-one (MIT).

18. The method according to claim 16, wherein the biocide is an oxidative biocide.

19. The method according to claim 18, wherein the biocide is an oxidative biocide selected from monochloramine (MCA), chlorine dioxide, performic acid, or an N-containing compound combined with an oxidant.

20. The method according to claim 1, wherein the fibrous web is a web of paper, board or tissue.

21. The method according to claim 1, wherein the intermediate residence entity is a storage tower or a broke tower.

* * * * *